(12) United States Patent
Mizuki

(10) Patent No.: US 8,507,900 B2
(45) Date of Patent: Aug. 13, 2013

(54) BENZOFLUORANTHENE DERIVATIVE AND ORGANIC ELECTROLUMINESCENCE ELEMENT COMPRISING SAME

(75) Inventor: Yumiko Mizuki, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 272 days.

(21) Appl. No.: 13/058,512

(22) PCT Filed: Aug. 12, 2009

(86) PCT No.: PCT/JP2009/064244
§ 371 (c)(1),
(2), (4) Date: Feb. 10, 2011

(87) PCT Pub. No.: WO2010/018842
PCT Pub. Date: Feb. 18, 2010

(65) Prior Publication Data
US 2011/0147732 A1    Jun. 23, 2011

(30) Foreign Application Priority Data
Aug. 12, 2008    (JP) .................. 2008-208053

(51) Int. Cl.
*H01L 29/08* (2006.01)
*H01L 35/24* (2006.01)

(52) U.S. Cl.
USPC ........................................... 257/40

(58) Field of Classification Search
None
See application file for complete search history.

(56) References Cited

U.S. PATENT DOCUMENTS
2006/0105198 A1    5/2006    Spindler et al.

FOREIGN PATENT DOCUMENTS

| | | |
|---|---|---|
| JP | 10-189247 | 7/1998 |
| JP | 10-294177 | 11/1998 |
| JP | 2005-068087 | 3/2005 |
| JP | 2008-305935 | 12/2008 |
| WO | WO-2008/120806 A1 | 10/2008 |
| WO | WO 2009/142314 | * 11/2009 |

OTHER PUBLICATIONS

International Search Report in PCT/JP2009/064244 dated Oct. 6, 2009.
Marcinow, et al. "Synthesis of 7,10-Bis(2-halophenyl)tribenzo[c,f,k]fluoranthene as a Potential Buckybowl Precursor", Journal of Organic Chemistry, 2000, vol. 65, No. 16, pp. 5063-5065.
Notice of Transmittal of Translation of the IPRP in PCT/JP2009/064244 dated Mar. 17, 2011.

* cited by examiner

*Primary Examiner* — Craig Ricci
(74) *Attorney, Agent, or Firm* — Foley & Lardner LLP

(57) ABSTRACT

A benzofluoranthene derivative represented by the following formula (1):

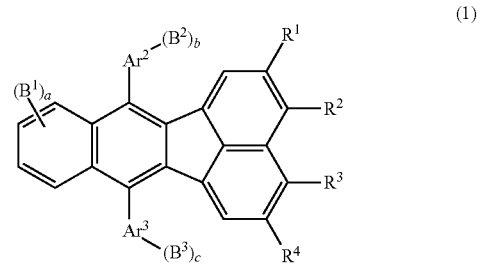

(1)

wherein at least one pair of "$R^1$ and $R^2$" and "$R^3$ and $R^4$" is bonded together to form a ring represented by the following formula (2):

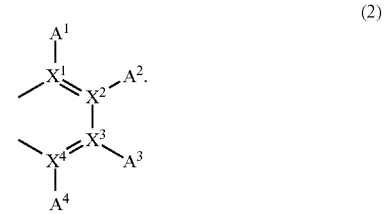

(2)

3 Claims, No Drawings

BENZOFLUORANTHENE DERIVATIVE AND ORGANIC ELECTROLUMINESCENCE ELEMENT COMPRISING SAME

TECHNICAL FIELD

The invention relates to a benzofluoranthene derivative, a material for an organic electroluminescence device comprising the same and an organic electroluminescence device using the same. More particularly, the invention relates to a benzofluoranthene derivative capable of fabricating an organic electroluminescence device having a high luminous efficiency and a long life.

BACKGROUND ART

An organic electroluminescence (EL) device is a self-emission device utilizing the principle that a fluorescent compound emits light by the recombination energy of holes injected from an anode and electrons injected from a cathode when an electric field is impressed. Such an organic EL device comprises a pair of electrodes, i.e. an anode and a cathode, and an organic light-emitting medium therebetween.

The organic light-emitting medium is formed of a stack of layers having each function. For example, it is a stack in which an anode, a hole-injecting layer, a hole-transporting layer, an emitting layer, and an electron-transporting layer and an electron-injecting layer are sequentially stacked.

As the emission material of the emitting layer, a material which emits light in each color (for example, red, green and blue) has been developed. For example, a fluoranthene compound is disclosed in Patent Document 1 and Patent Document 2 as a blue-emitting compound.

However, the fluoranthene compound disclosed in Patent Document 1 and Patent Document 2 has a problem that it is not satisfactory in respect of luminous efficiency and lifetime.
[Patent Document 1] JP-A-H10-189247
[Patent Document 2] JP-A-2005-068087

DISCLOSURE OF THE INVENTION

The object of the invention is to provide a benzofluoranthene derivative capable of fabricating an organic EL device having a high luminous efficiency and a long life.

According to the invention, the following benzofluoranthene derivative or the like is provided.
1. A benzofluoranthene derivative represented by the following formula (1):

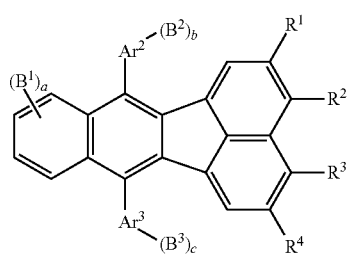

(1)

wherein $B^1$ to $B^3$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxyl group, a substituted or unsubstituted silyl group, a carboxy group, or a halogen atom;

a is an integer of 0 to 4, b and c are independently an integer of 0 to 5, when a is 2 or more, $B^1$s may be the same or different, and they may be bonded together to form a saturated or unsaturated ring, when b is 2 or more, $B^2$s may be the same or different, and they may be bonded together to form a saturated or unsaturated ring, when c is 2 or more, $B^3$s may be the same or different, and they may be bonded together to form a saturated or unsaturated ring, $Ar^2$ and $Ar^3$ are independently a substituted or unsubstituted aryl group having 5 to 50 ring carbon atoms, or a substituted or unsubstituted heterocyclic group having 5 to 50 ring carbon atoms, $R^1$ to $R^4$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxy group, a substituted or unsubstituted silyl group, a carboxy group, or a halogen atom;

at least one pair of "$R^1$ and $R^2$" and "$R^3$ and $R^4$" is bonded together to form a ring represented by the following formula (2), when both "$R^1$ and $R^2$" and "$R^3$ and $R^4$" form a ring, the rings they form may be the same or different,

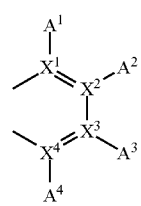

(2)

wherein $A^1$ to $A^4$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxyl group, a substituted or unsubstituted silyl group, a carboxy group, or a halogen atom;

among $A^1$ to $A^4$, adjacent groups may be bonded to form a saturated or unsaturated ring, and the ring may have a substituent, and $X^1$ to $X^4$ are independently a carbon atom or a nitrogen atom, and when any one of $X^1$ to $X^4$ is a nitrogen atom, $A^1$ to $A^4$ which bond to the one of $X^1$ to $X^4$ do not exist.

2. The benzofluoranthene derivative according to 1 wherein $R^1$ and $R^2$ are bonded together to form the ring represented by formula (2).

3. The benzofluoranthene derivative according to 1 or 2 wherein $R^1$ and $R^2$, and $R^3$ and $R^4$ independently form the ring represented by formula (2), and the ring which $R^1$ and $R^2$ form is different from the ring which $R^3$ and $R^4$ form.

4. The benzofluoranthene derivative according to 1 or 2 wherein $R^1$ and $R^2$, and $R^3$ and $R^4$ independently form the ring represented by formula (2), and the ring which $R^1$ and $R^2$ form is the same as the ring which $R^3$ and $R^4$ form.

5. The benzofluoranthene derivative according to any one of 1 to 4 wherein $A^1$ and $A^2$ are bonded together to form a saturated or unsaturated ring.

6. The benzofluoranthene derivative according to any one of 1 to 5 wherein $A^1$ and $A^2$, and $A^3$ and $A^4$ are bonded together to form a saturated or unsaturated ring.

7. The benzofluoranthene derivative according to any one of 1 to 4 wherein $A^2$ and $A^3$ are bonded together to form a saturated or unsaturated ring.

8. The benzofluoranthene derivative according to any one of 1 to 4 wherein $A^1$ to $A^4$ are independently a hydrogen atom, an alkyl group having 1 to 4 carbon atoms, or an aryl group having 6 to 10 carbon atoms.

9. The benzofluoranthene derivative according to any one of 1 to 8 wherein all of $X^1$ to $X^4$ are a carbon atom.

10. The benzofluoranthene derivative according to any one of 1 to 8 wherein one or two of $X^1$ to $X^4$ are a nitrogen atom.

11. The benzofluoranthene derivative according to any one of 1 to 10 wherein $Ar^2$ and $Ar^3$ are independently a phenyl group or a naphthyl group.

12. The benzofluoranthene derivative according to any one of 1 to 11 wherein $B^1$ to $B^3$ are independently a hydrogen atom, an alkyl group having 1 to 4 carbon atoms, an aryl group having 6 to 10 carbon atoms, or a substituted or unsubstituted heterocyclic group having 5 to 50 ring carbon atoms, and a, b and c are independently an integer of 1 or 2.

13. A material for an organic electroluminescence device comprising the benzofluoranthene derivative according to any one of 1 to 12.

14. The material for an organic electroluminescence device according to 13, which is a doping material.

15. An organic electroluminescence device comprising one or more organic thin layers comprising an emitting layer, between a cathode and an anode, and at least one of the organic thin layers comprising the material for an organic electroluminescence device according to 13 or 14.

16. The organic electroluminescence device according to 15 wherein the emitting layer comprises the material for an organic electroluminescence device, and the content of the benzofluoranthene derivative is 0.1 to 20 wt %.

17. The organic electroluminescence device according to 15 or 16, which can emit blue light.

According to the invention, a benzofluoranthene derivative capable of fabricating an organic EL device which has a high luminous efficiency and a long life can be provided.

Further, according to the invention, an organic EL device which has a high luminous efficiency and a long life can be provided.

BEST MODE FOR CARRYING OUT THE INVENTION

The benzofluoranthene derivative of the invention is represented by the following formula (1):

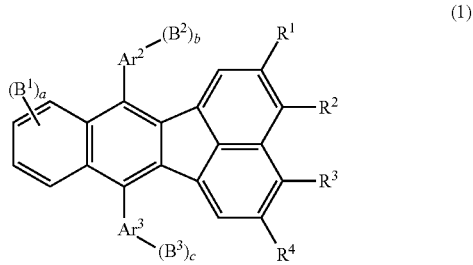

wherein $B^1$ to $B^3$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxyl group, a substituted or unsubstituted silyl group, a carboxy group, or a halogen atom;

a is an integer of 0 to 4, b and c are independently an integer of 0 to 5, when a is an integer of 2 or more, $B^1$s may be the same or different, and they may be bonded together to form a saturated or unsaturated ring, when b is an integer of 2 or more, $B^2$s may be the same or different, and they may be bonded together to form a saturated or unsaturated ring, when c is an integer of 2 or more, $B^3$s may be the same or different, and they may be bonded together to form a saturated or unsaturated ring, $Ar^2$ and $Ar^3$ are independently a substituted or unsubstituted aryl group having 5 to 50 ring carbon atoms, or a substituted or unsubstituted heterocyclic group having 5 to 50 ring carbon atoms, $R^1$ to $R^4$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxyl group, a substituted or unsubstituted silyl group, a carboxy group, or a halogen atom;

at least one pair of "$R^1$ and $R^2$" and "$R^3$ and $R^4$" is bonded together to form a ring represented by the following formula (2), when both "$R^1$ and $R^2$" and "$R^3$ and $R^4$" form a ring, the rings they form may be the same or different,

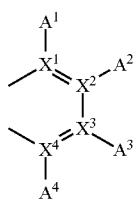
(2)

wherein $A^1$ to $A^4$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxyl group, a substituted or unsubstituted silyl group, a carboxy group, or a halogen atom;

among $A^1$ to $A^4$, adjacent groups may be bonded to form a saturated or unsaturated ring, and the ring may have a substituent, and $X^1$ to $X^4$ are independently a carbon atom or a nitrogen atom, and when any one of $X^1$ to $X^4$ is a nitrogen atom, $A^1$ to $A^4$ which bond to the one of $X^1$ to $X^4$ do not exist.

Due to its widely conjugated structure, the benzofluoranthene derivative of the invention can enhance the luminous efficiency and prolong the lifetime of an organic EL device when used as a material for an organic EL device.

In respect of durability, the benzofluoranthene derivative of the invention is preferably a benzofluoranthene derivative which is represented by the following formula (1-1) or a benzofluoranthene derivative which is represented by the following formula (1-2):

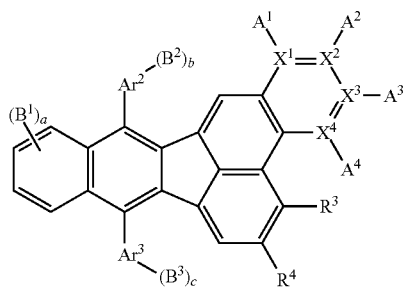
(1-1)

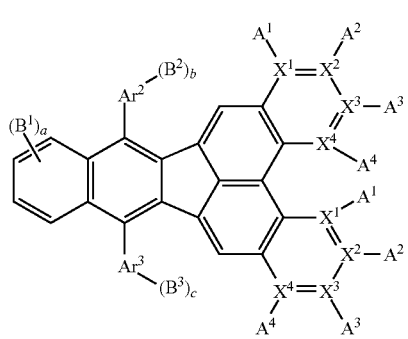
(1-2)

The substituents of the formula (1-1) and the formula (1-2) are the same as those in the formula (1) and the formula (2).

The benzofluoranthene derivative of the formula (1-1) is a benzofluoranthene derivative of the formula (1) in which $R^1$ and $R^2$ are bonded together to form the ring of the formula (2). The benzofluororanthene derivative of the formula (1-2) is a benzofluoranthene derivative of the formula (1) in which $R^1$ and $R^2$, and $R^3$ and $R^4$, are respectively bonded to form the ring of the formula (2).

The benzofluoranthene derivative of the formula (1-2) has two of the rings of the formula (2). These rings may be the same or different.

In respect of the adjustment of chromaticity, in the ring of the formula (2), it is preferred that $A^1$ and $A^2$ be bonded together to form a saturated or unsaturated ring. It is more preferred that $A^3$ and $A^4$ be bonded together to form a saturated or unsaturated ring.

In respect of durability, in the ring of the formula (2), it is preferred that $A^2$ and $A^3$ be bonded together to form a saturated or unsaturated ring.

In respect of stability, $A^1$ to $A^4$ which do not form a ring is preferably a hydrogen atom, an alkyl group having 1 to 4 carbon atoms or an aryl group having 6 to 10 carbon atoms.

As the saturated or unsaturated ring formed by $A^1$ and $A^2$, $A^3$ and $A^4$, and $A^2$ and $A^3$, a phenyl ring, a naphthyl ring, an anthracenyl group, a cyclopentyl group, a cyclohexyl group, a cycloheptyl group, a heterocyclic ring or the like can be given. Of these rings, a phenyl ring and a naphthyl ring are preferable in respect of stability.

The saturated or unsaturated ring formed by adjacent groups of $A^1$ to $A^4$ may further have a substituent. The substituents for the saturated or unsaturated ring are the same as those for $A^1$ to $A^4$.

Specific examples of the benzofluoranthene derivative in which $A^1$ to $A^4$ from a ring are given below.

A benzofluoranthene derivative represented by the formula (1-1) in which $A^1$ and $A^2$ form a phenyl ring (formula 1-1-1);

A benzofluoranthene derivative represented by the formula (1-1) in which $A^2$ and $A^3$ form a phenyl ring (formula 1-1-2);

A benzofluoranthene derivative represented by the formula (1-1) in which $A^3$ and $A^4$ form a phenyl ring (formula 1-1-3); and A benzofluoranthene derivative represented by the formula (1-1) in which $A^1$ and $A^2$, and $A^3$ and $A^4$ form a phenyl ring (formula 1-1-4).

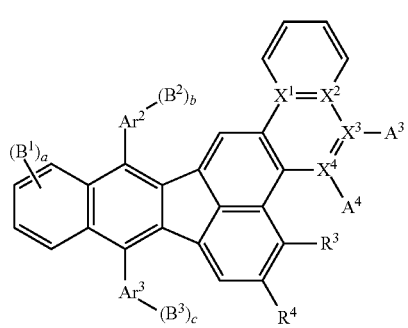
(1-1-1)

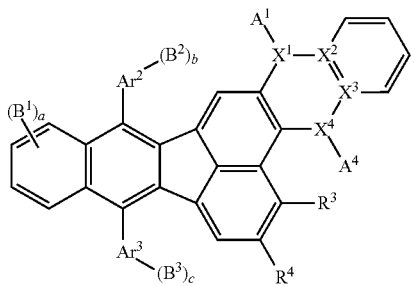

(1-1-2)

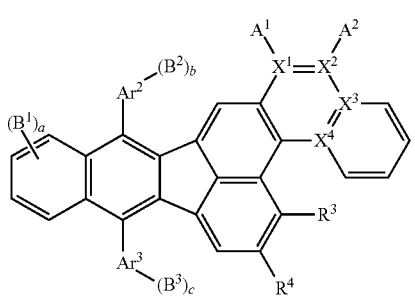

(1-1-3)

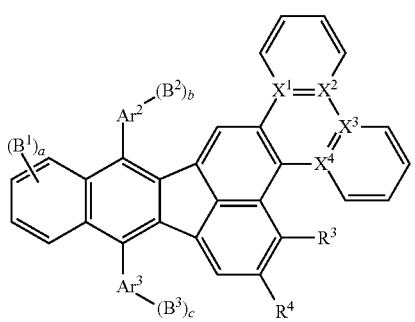

(1-1-4)

(the substituents of the formulas 1-1-1 to 1-1-4 are the same as those of the formulas (1) and (2)).

In respect of adjustment of chromaticity, it is preferred that all of $X^1$ to $X^4$ of the rings of the formula (2) be a carbon atom, or that any one or two are a nitrogen atom.

In respect of stability, $Ar^2$ and $Ar^3$ in the formula (1) are a phenyl group or a naphthyl group, respectively.

In respect of durability, in the benzofluoranthene derivative of the formula (1), it is preferred that $B^1$ to $B^3$ be independently a hydrogen atom, an alkyl group having 1 to 4 carbon atoms or an aryl group having 1 to 6 carbon atoms, and a, b and c are independently an integer of 1 or 2.

$B^2$ and $B^3$ are independently a substituent of $Ar^2$ and $Ar^3$.

The substituent of the benzofluoranthene derivative of the invention will be explained below. In the invention, the "ring carbon atoms" mean carbon atoms which constitute a saturated ring, an unsaturated ring or an aromatic ring. The "ring atoms" mean carbon atoms and hetero atoms which constitute a heterocyclic ring (including a saturated ring, an unsaturated ring and an aromatic ring). For example, in the case of a phenyl group substituted by a naphthyl group, it means a substituted aryl group having 16 ring carbon atoms, and in the case of a phenyl group substituted by a methyl group, it means a substituted aryl group having 6 ring carbon atoms.

The substituted or unsubstituted alkyl group having 1 to 50 carbon atoms represented by $B^1$ to $B^3$, $A^1$ to $A^4$ and $R^1$ to $R^4$ include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloromethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a trifluoromethyl group, a perfluoroethyl group, a perfluoropropyl group, a perfluorobutyl group, a perfluoropentyl group, a perfluorohexyl group, a 1H,1H-perfluoroethyl group, a 1H,1H-perfluoropropyl group, a 1H,1H-perfluorobutyl group, a 1H,1H-perfluoropentyl group and a 1H,1H-perfluorohexyl group.

A substituted or unsubstituted alkyl group having 1 to 20 carbon atoms is preferable.

Examples of the substituted or unsubstituted aryl group having 5 to 50 ring carbon atoms of $B^1$ to $B^3$, $A^1$ to $A^4$ and $R^1$ to $R^4$ include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

A substituted or unsubstituted aryl group having 6 to 20 ring atoms is preferable.

As the substituted or unsubstituted heterocyclic group having 5 to 50 ring carbon atoms, residues such as imidazole, benzoimidazole, pyrrole, furan, thiophene, benzothiophene, oxadiazoline, indoline, carbazole, pyridine, quinoline, benzoquinoline, pyralozine, imidazolidine, piperidine, dibenzofuran, benzofuran, dibenzothiophene or the like can be given.

As the substituted or unsubstituted aralkyl group having 6 to 50 ring carbon atoms represented by $B^1$ to $B^3$, $A^1$ to $A^4$ and $R^1$ to $R^4$, a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphtylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl, or the like can be given, for example.

A substituted or unsubstituted aralkyl group having 7 to 20 carbon atoms is preferable.

As the substituted or unsubstituted cycloalkyl group having 3 to 50 ring carbon atoms represented by $B^1$ to $B^3$, $A^1$ to $A^4$ and $R^1$ to $R^4$, a cylopropyl group, a cyclobutyl group, a cyclopentyl group, a cyclohexyl group, a 4-methylcyclohexyl group, a 1-adamantyl group, a 2-adamantyl group, a 1-norbonyl group, a 2-norbonyl group or the like can be given.

A substituted or unsubstituted cycloalkyl group having 5 to 10 carbon atoms is preferable.

The substituted or unsubstituted alkoxy group having 1 to 50 carbon atoms represented by $B^1$ to $B^3$, $A^1$ to $A^4$ and $R^1$ to $R^4$ is a group represented by —OY. As examples of Y, the same examples as those for the substituted or unsubstituted alkyl group having 1 to 50 carbon atoms represented by $B^1$ to $B^3$, $A^1$ to $A^4$ and $R^1$ to $R^4$ can be given.

A substituted or unsubstituted alkoxy group having 1 to 20 carbon atoms is preferable.

The substituted or unsubstituted aryloxy group having 5 to 50 carbon atoms represented by $B^1$ to $B^3$, $A^1$ to $A^4$ and $R^1$ to $R^4$ is a group represented by —OY'. As examples of Y', the same examples as those for the substituted or unsubstituted aryloxy group having 5 to 50 ring carbon atoms represented by $B^1$ to $B^3$, $A^1$ to $A^4$ and $R^1$ to $R^4$ can be given.

A substituted or unsubstituted aryloxy group having 5 to 20 ring atoms is preferable.

As the substituent which further substitutes the substituent of the above-mentioned benzofluoranthene derivative (for example, a substituent for the substituted or unsubstituted alkyl group having 1 to 50 carbon atoms), an aryl group having 5 to 50 ring carbon atoms, an alkyl group having 1 to 50 carbon atoms, an alkoxy group having 1 to 50 carbon atoms, an aralkyl group having 6 to 50 ring carbon atoms, an aryloxy group having 5 to 50 ring carbon atoms, an arylthio group having 5 to 50 ring carbon atoms, an alkoxycarbonyl group having 1 to 50 carbon atoms, an amino group, a halogen atom, a cyano group, a nitro group, a hydroxyl group, a carboxy group or the like can be given. Specific examples of the substituent are the same as the specific examples of each group in the formulas (1) and (2).

Specific examples of the benzofluoranthene derivative of the invention are given below.

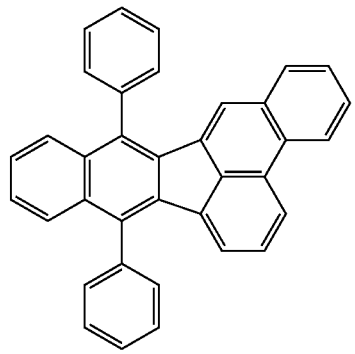

D-1

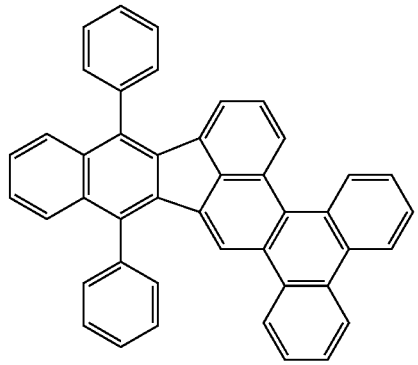

D-2

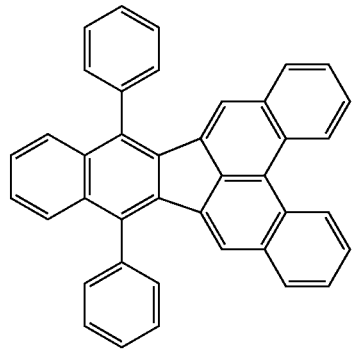

D-3

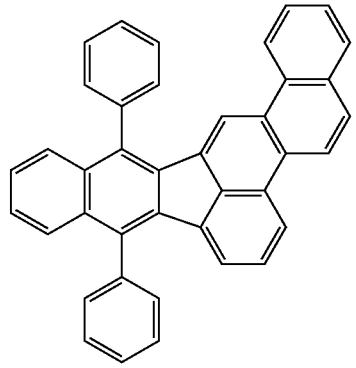

D-4

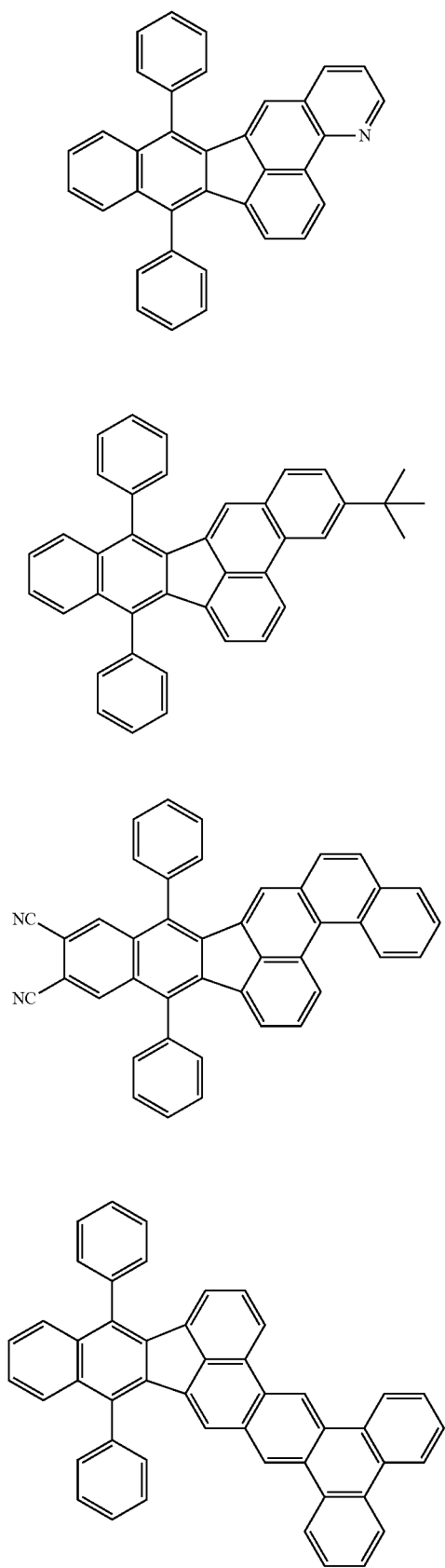
D-5
D-6
D-7
D-8
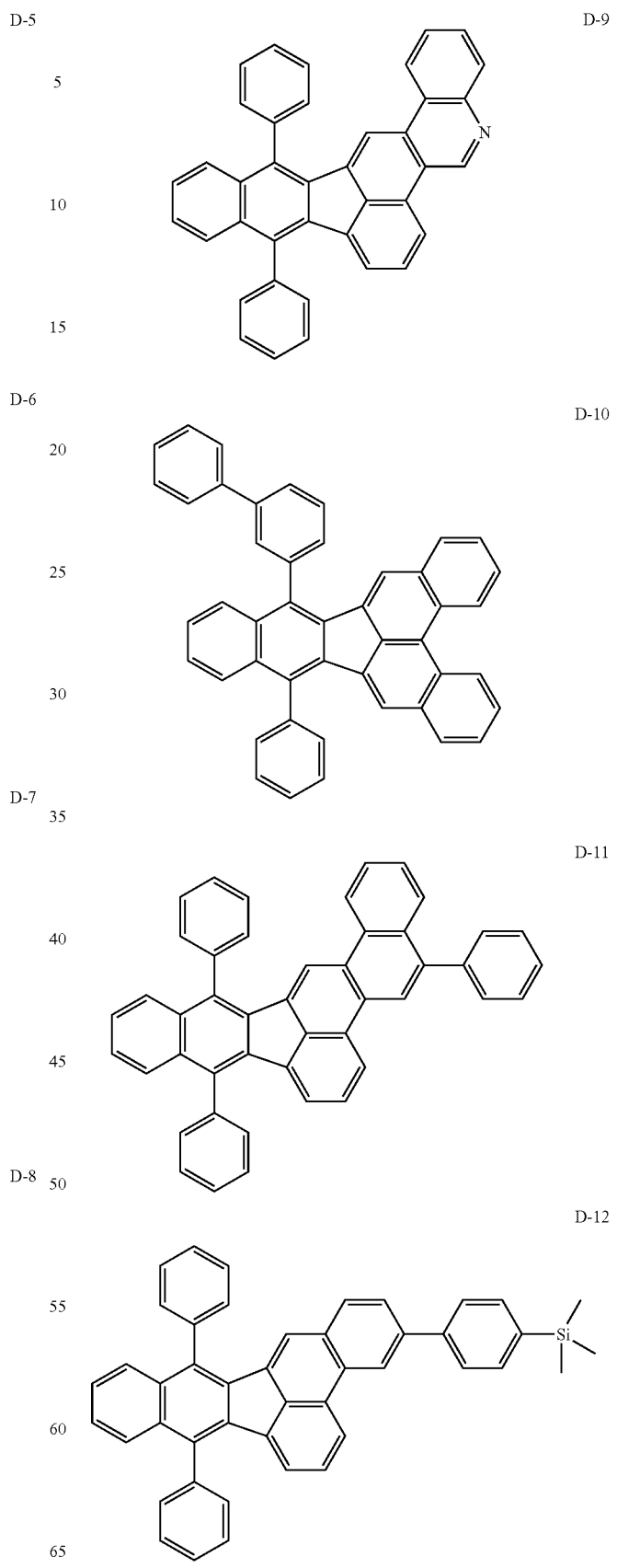
D-9
D-10
D-11
D-12

-continued
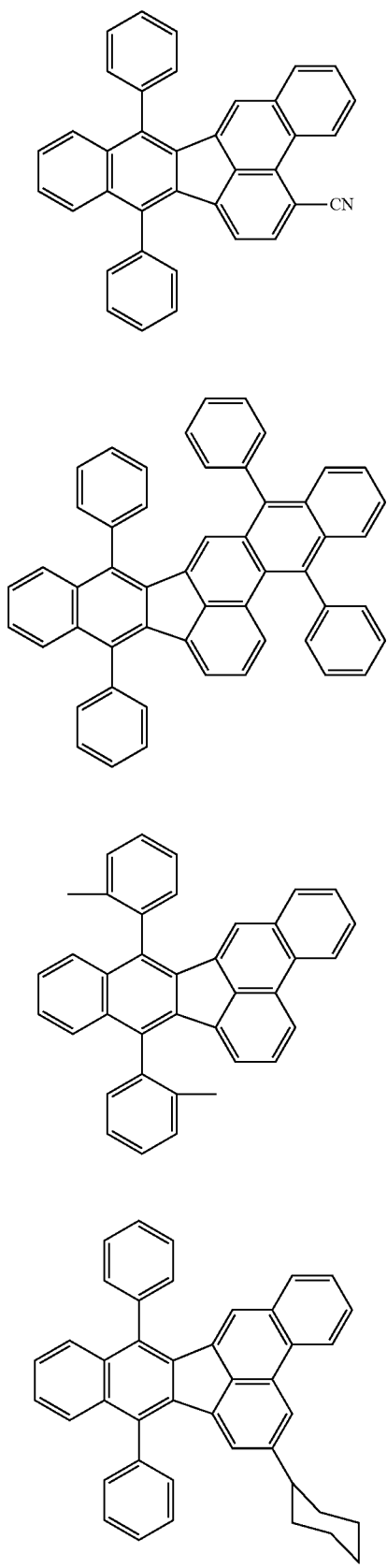
D-13
D-14
D-15
D-16
-continued
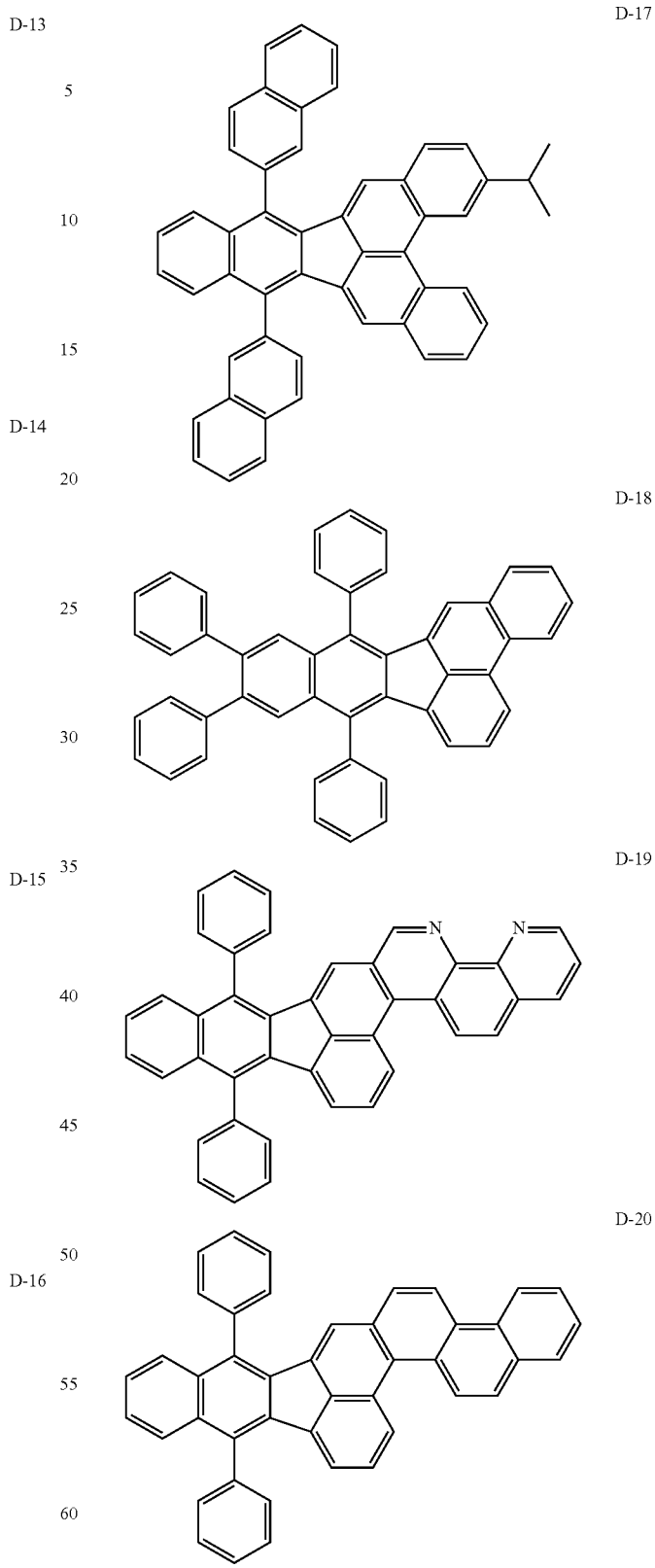
D-17
D-18
D-19
D-20
The benzofluororanthene derivative of the invention can be synthesized by a method described in J. Org. Chem., 55, 4190 (1990), J. Org. Chem., 68, 883 (2003) or by a carbon-carbon bond generation reaction (Suzuki reaction, Kumada-Tamao coupling reaction, Still reaction, Sonogashira reaction, or the like) and an annulation reaction.

It is preferred that the benzofluoranthene derivative of the invention be used as a material for an organic EL device. It is particularly preferable to use it as an emitting material for an organic EL device, especially as a doping material.

Regarding the organic EL device of the invention, in an organic electroluminescence device in which organic compound layers comprising one layer or a plurality of layers containing at least an emitting layer between a pair of electrodes, at least one of the above-mentioned organic compound layers comprises the benzofluoranthene derivative of the invention.

In the organic EL device of the invention, it is preferred that the emitting layer contain a benzofluoranthene derivative. The emitting layer contain the benzofluoranthene derivative of the invention preferably in an amount of 0.1 to 20 wt %, further preferably 0.5 to 20 wt %, particularly preferably 1 to 18 wt % and most preferably 2.5 to 15 wt %.

The organic EL device using the material for an organic EL device containing the benzofluoranthene derivative of the invention can emit blue light.

When the benzofluoranthene derivative of the invention is used as an emitting material of the organic EL device, it is preferred that the emitting layer contain at least one kind of the benzofluoranthene derivative and at least one kind selected from the compounds represented by the formulas (2a), (2b), (2c) and (2d). It is preferred that at least one kind selected from the compounds represented by the following formulas (2a), (2b), (2c) and (2d) be a host material.

An explanation will be made on the compounds represented by the formulas (2a), (2b), (2c) and (2d).

Formula (2a)

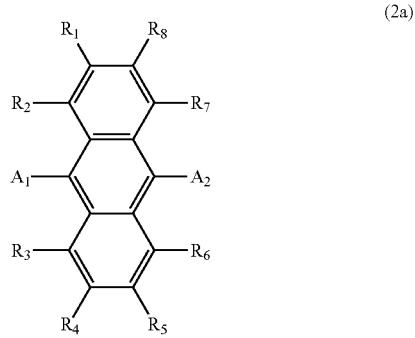

(2a)

In the formula (2a), $A^1$ and $A^2$ are independently a group induced from a substituted or unsubstituted aromatic ring having 6 to 20 ring carbon atoms. The aromatic ring may be substituted by one or two or more substituents. The substituent is selected from a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxy group, a halogen atom, a cyano group, a nitro group and a hydroxyl group. If the above-mentioned aromatic ring is substituted by two or more substituents, the substituents may be the same or different, and adjacent substituents may be bonded together to form a saturated or unsaturated ring structure.

$R_1$ to $R_8$ are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxy group, a halogen atom, a cyano group, a nitro group and a hydroxyl group.

In the formula (2a), it is preferred that $A_1$ and $A_2$ mentioned above be different groups.

In the formula (2a), it is preferred that at least one of $A_1$ and $A_2$ be a substituent having a substituted or unsubstituted fused ring group having 10 to 30 ring atoms.

It is preferred that the above-mentioned substituted or unsubstituted fused ring group having 10 to 30 ring atoms be a naphthalene ring.

The substituted or unsubstituted aryloxy group and arylthio group having 5 to 50 ring atoms for $R^1$ to $R^8$ and the substituent of the aromatic ring in the formula (2a) are represented by —OY' and —SY", respectively. Examples of —Y' and Y" include the same examples as those for the substituted or unsubstituted aryl group having 6 to 50 ring atoms of the substituent of $R_1$ to $R_8$ and the aromatic ring.

The substituted or unsubstituted alkoxycarbonyl group having 1 to 50 carbon atoms for $R_1$ to $R_8$ and the substituent of the aromatic ring in the formula (2a) is represented by —COOZ. Examples of Z include the same examples as those of the substituted or unsubstituted alkyl group having 1 to 50 carbon atoms for $R_1$ to $R_8$ and the substituent of the aromatic ring.

Examples of the silyl group for $R_1$ to $R_8$ and the substituent of the aromatic ring in the formula (2a) include a trimethylsilyl group, a triethylsilyl group, a t-butyldimethylsilyl group, a vinyldimethylsilyl group, a propyldimethylsilyl group and a triphenylsilyl group.

As the halogen atom for $R_1$ to $R_8$ and the substituent of the aromatic ring in the formula (2a), fluorine or the like can be given.

As the substituent for $R_1$ to $R_8$ and the substituent for the aromatic ring, a halogen atom, a hydroxyl group, a nitro group, a cyano group, an alkyl group, an aryl group, a cycloalkyl group, an alkoxy group, an aromatic heterocyclic group, an aralkyl group, an aryloxy group, an arylthio group, an alkoxycarbonyl group, a carboxy group or the like can be given.

It is preferred that the anthracene derivative represented by the formula (2a) be a compound having a structure shown by the following formula (2a').

(2a')

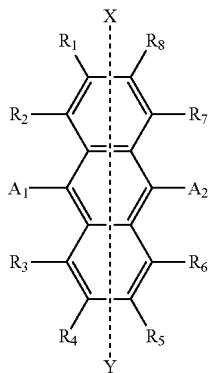

In the formula (2a'), $A_1$ and $A_2$, $R_1$ to $R_8$ are independently the same as that in the formula (2a), and the same specific examples can be given, provided that groups do not symmetrically bond to $9^{th}$ and $10^{th}$ positions of the central anthracene with respect to X-Y axis.

Specific examples of the anthracene derivative to be used in the organic EL device of the invention, represented by the formula (2a) include known various anthracene derivatives such as those having two anthracene skeletons in the molecule shown in JP-A-2004-356033, [0043] to [0063] and compounds having one anthracene skeleton shown in WO2005/061656, pages 27 to 28.

Formula (2b)

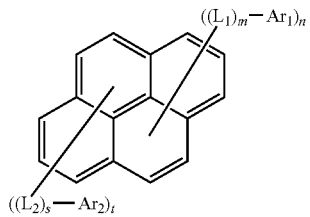

(2b)

In the formula (2b), $Ar_1$ and $Ar_2$ are independently a substituted or unsubstituted aryl group having 6 to 50 ring carbon atoms.

$L_1$ and $L_2$ are independently selected from a substituted or unsubstituted phenylene group, a substituted or unsubstituted naphthalenylene group, a substituted or unsubstituted fluorenylene group and a substituted or unsubstituted dibenzosilolylene group.

m is an integer of 0 to 2, n is an integer of 1 to 4, s is an integer of 0 to 2 and t is an integer of 0 to 4.

$L_1$ or $Ar_1$ bonds to any position of the $1^{st}$ to $5^{th}$ positions of pyrene, and $L_2$ or $Ar_2$ bonds to any position of the $6^{th}$ to $10^{th}$ positions of pyrene.

$L_1$ and $L_2$ in the formula (2b) are preferably selected from a substituted or unsubstituted phenylene group and a substituted or unsubstituted fluorenylene group.

As the substituent thereof, substituents similar to those exemplified in the above-mentioned aromatic ring group can be given.

m in the formula (2b) is preferably an integer of 0 to 1, and n in the formula (2b) is preferably an integer of 1 to 2. s in the formula (2b) is preferably an integer of 0 to 1.

t in the formula (2b) is preferably an integer of 0 to 2.

Formula (2c)

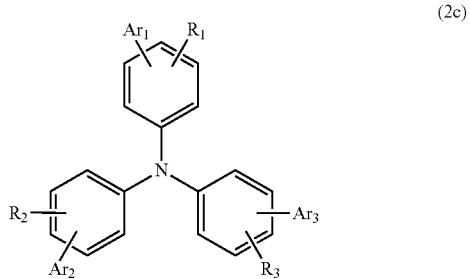

(2c)

In the formula (2c), $Ar_1$, $Ar_2$ and $Ar_3$ are independently selected from a group having an anthracene structure, a group having a phenanthrene structure, a group having a perylene structure and a group having a pyrene structure.

$R_1$, $R_2$ and $R_3$ are independently a hydrogen atom or a substituent.

$Ar_1$, $Ar_2$ and $Ar_3$ in the formula (2c) is preferably selected from a substituted or unsubstituted anthrylphenyl group, an anthryl group, a phenanthrenyl group, a perylenyl group and a pyrenyl group, more preferably selected from an alkyl-substituted or unsubstituted anthrylphenyl group and a pyrenyl group, and particularly preferably selected from a pyrenyl group and a phenanthrenyl group.

Examples of $R_1$, $R_2$ and $R_3$ in the formula (2c) include a hydrogen atom, an alkyl group (preferably one having 1 to 30 carbon atoms, more preferably 1 to 20 carbon atoms, and particularly preferably 1 to 10 carbon atoms; specific examples thereof include methyl, ethyl, isopropyl, t-butyl, n-octyl, n-decyl, n-hexadecyl, cyclopropyl, cyclopentyl and cyclohexyl), an alkenyl group (preferably one having 2 to 30 carbon atoms, more preferably 2 to 20 carbon atoms, and particularly preferably 2 to 10 carbon atoms; specific examples thereof include vinyl, allyl, 2-butenyl and 3-pentenyl), an alkynyl group (preferably one having 2 to 30 carbon atoms, more preferably 2 to 20 carbon atoms, and particularly preferably 2 to 10 carbon atoms; specific examples thereof include propargyl and 3-pentynyl), an aryl group (preferably one having 6 to 30 carbon atoms, more preferably 6 to 20 carbon atoms, and particularly preferably one having 6 to 12 carbon atoms; the specific examples thereof include phenyl, p-methylphenyl, naphthyl and anthranyl), an amino group (preferably one having 0 to 30 carbon atoms, more preferably 0 to 20 carbon atoms, and particularly preferably 0 to 10 carbon atoms; the specific examples thereof include amino, methylamino, dimethylamino and diethylamino, dibenzylamino, diphenylamino and ditolylamino group), an alkoxy group (preferably one having 1 to 30 carbon atoms, more preferably 1 to 20 carbon atoms, and particularly preferably 1 to 10 carbon atoms; the specific examples thereof include methoxy, ethoxy, butoxy, and 2-ethylhexyloxy), an aryloxy group (preferably one having 6 to 30 carbon atoms, more preferably 6 to 20 carbon atoms, and particularly preferably 6 to 12 carbon atoms; the specific examples thereof include phenyloxy, 1-naphthyloxy and 2-naphthyloxy), a heteroaryloxy group (preferably one having 1 to 30 carbon atoms, more preferably 1 to 20 carbon atoms, and particularly preferably 1 to 12 carbon atoms; the specific examples thereof include pyridyloxy, pyrazyloxy, pyrimidyloxy and quinolyloxy); an acyl group (preferably one having 1 to 30 carbon atoms, more preferably 1 to 20 carbon atoms, and particularly preferably 1 to 12 carbon atoms; the specific examples thereof include acetyl, benzoyl, formyl and pivaloyl), an alkoxycarbonyl group (preferably one having 2 to 30 carbon atoms, more preferably 2 to 20 carbon atoms, and particularly preferably 2 to 12 carbon atoms; the specific examples thereof include methoxycarbonyl and ethoxycarbonyl); an aryloxycarbonyl group (preferably one having 7 to 30 carbon atoms, more preferably 7 to 20 carbon atoms and particularly preferably 7 to 12 carbon atoms; the specific examples thereof include phenyloxycarbonyl); an acyloxy group (preferably one having 2 to 30 carbon atoms, more preferably 2 to 20 carbon atoms and particularly preferably 2 to 10 carbon atoms; the specific examples thereof include acetoxy and benzoyloxy), an acylamino group (preferably one having 2 to 30 carbon atoms, more preferably 2 to 20 carbon atoms, and particularly preferably 2 to 10 carbon atoms; the specific examples thereof include acetylamino and benzoylamino), an alkoxycarbonylamino group (preferably one having 2 to 30 carbon atoms, more preferably 2 to 20 carbon atoms, and particularly preferably 2 to 12 carbon atoms; the specific examples thereof include methoxycarbonylamino), an aryloxycarbonylamino group (preferably one having 7 to 30 carbon atoms, more preferably 7 to 20 carbon atoms, particularly preferably 7 to 12 carbon atoms; the specific examples thereof include phenyloxycarbonylamino), a sulfonylamino group (preferably one having 1 to 30 carbon atoms, more preferably one having 1 to 20 carbon atoms and particularly preferably one having 1 to 12 carbon atoms; the specific examples thereof include methanesulfonylamino and benzenesulfonylamino), a sulfamoylamino group (preferably one having 0 to 30 carbon atoms, more preferably 0 to 20 carbon atoms and particularly preferably 0 to 12 carbon atoms; the specific examples thereof include sulfamoyl, methylsulfamoyl, dimethylsulfamoyl and phenylsulfamoyl), a carbamoyl group (preferably one having 1 to 30 carbon atoms, more preferably one having 1 to 20 carbon atoms and particularly preferably one having 1 to 12 carbon atoms; the specific examples thereof include carbamoyl, methylcarbamoyl, diethylcarbamoyl and phenylcarbamoyl), an alkylthio group (preferably one having 1 to 30 carbon atoms, more preferably 1 to 20 carbon atoms and particularly preferably 1 to 12 carbon atoms; the specific examples include methylthio and ethylthio), an arylthio group (preferably one having 6 to 30 carbon atoms, more preferably one having 6 to 20 carbon atoms and particularly preferably one having 6 to 12 carbon atoms; the specific examples thereof include phenylthio), a heteroarylthio group (preferably one having 1 to 30 carbon atoms, more preferably one having 1 to 20 carbon atoms, and particularly preferably one having 1 to 12 carbon atoms; the specific examples thereof include pyridylthio, 2-benzoimidazolylthio, 2-benzoxazolylthio and 2-benzothiazolylthio); a sulfonyl group (preferably one having 1 to 30 carbon atoms, more preferably 1 to 20 carbon atoms and particularly preferably 1 to 12 carbon atoms; the specific examples thereof include mesyl and tosyl); a sulfinyl group (preferably one having 1 to 30 carbon atoms, more preferably 1 to 20 carbon atoms and particularly preferably 1 to 12 carbon atoms; the specific examples thereof include methanesulfinyl and benzenesulfinyl), an ureido group (preferably one having 1 to 30 carbon atoms, more preferably 1 to 20 carbon atoms and particularly preferably 1 to 12 carbon atoms; the specific examples thereof include ureido, methylureido and phenylureido), a phosphoric amide group (preferably one having 1 to 30 carbon atoms, more preferably 1 to 20 carbon atoms and particularly preferably 1 to 12 carbon atoms; the specific examples thereof include diethylphosphoric amide and phenylphosphatoric amide), a hydroxyl group, a mercapto group, a halogen atom (for example, a fluorine atom, a chlorine atom, a bromine atom, an iodine atom or the like can be given), a cyano group, a sulfo group, a carboxy group, a nitro group, a hydroxamic acid group, a sulfino group, a hydrazino group, an imino group, a heterocyclic group (preferably one having 1 to 30 carbon atoms, more preferably 1 to 12 carbon atoms, and as the hetero atom, a nitrogen atom, an oxygen atom and a sulfur atom can be given, the specific examples thereof include imidazolyl, pyridyl, quinolyl, furyl, thienyl, piperidyl, morpholino, benzoxazolyl, benzimidazolyl, and benzothiazolyl can be given), and a substituted or unsubstituted silyl group (preferably one having 3 to 40 carbon atoms, more preferably 3 to 30 carbon atoms and particularly preferably 3 to 24 carbon atoms; the specific examples thereof include trimethylsilyl and triphenylsilyl). These substituents may further be substituted.

$R_1$, $R_2$ and $R_3$ in the formula (2c) are preferably selected from an alkyl group and an aryl group.

Specific examples of the amine derivative to be used in the organic EL device of the invention represented by the formula (2c) include known various amine derivatives such as those shown in JP-A-2002-324678 [0079] to [0083].

Formula (2d)

(2d)

In the formula (2d), $Ar_{11}$, $Ar_{21}$ and $Ar_{31}$ are independently an aryl group having 6 to 50 ring carbon atoms. The aryl group may be substituted by one or two or more substituents.

At least one of $Ar_{11}$, $Ar_{21}$ and $Ar_{31}$ and the substituents of these aryl groups has a fused ring aryl structure having 10 to 20 ring carbon atoms or a fused ring heteroaryl structure having 6 to 20 ring carbon atoms.

Ar is a trivalent group induced from the aromatic ring or the heterocyclic aromatic ring.

The aryl group having 6 to 50 ring carbon atoms of $Ar_{11}$, $Ar_{21}$ and $Ar_{31}$ in the formula (2d) preferably has 6 to 30, more preferably 6 to 20, further preferably 6 to 16 ring carbon atoms. These aryl groups may further have a substituent.

Examples of the substituent on the aryl group include an alkyl group, an alkenyl group, an alkynyl group, an aryl group, an amino group, an alkoxy group, an aryloxy group, a heteroaryloxy group, an acyl group, an alkoxycarbonyl group, an aryloxycarbonyl group, an acyloxy group, an acylamino group, an alkoxycarbonylamino group, an aryloxy carbonylamino group, a sulfonylamino group, a sulfamoyl group, a carbamoyl group, an alkylthio group, an arylthio group, a heteroarylthio group, a sulfonyl group, a sulfinyl group, an ureido group, a phosphoric amide group, a hydroxy group, a mercapto group, a halogen atom (for example, a fluorine atom, a chlorine atom, a bromine atom, an iodine atom, etc. can be given), a cyano group, a sulfo group, a carboxy group, a nitro group, a hydroxamic acid group, a sulfino group, a hydrazino group, an imino group, a heterocyclic group, a silyl group, etc. can be given. These substituents may be further substituted.

As the fused ring aryl structure having 10 to 20 ring carbon atoms of at least one of $Ar_{11}$, $Ar_{21}$, $Ar_{31}$ and the substituent of these aryl groups in the formula (2d), a naphthalene structure, an anthracene structure, a phenanthrene structure, a pyrene structure and a perylene structure or the like can be given. Of these, a naphthalene structure, an anthracene structure, a pyrene structure and a phenanthrene structure are preferable. A phenanthrene structure and an aryl structure with four or more rings are preferable, with a pyrene structure being particularly preferable.

As the fused ring heteroaryl structure having 6 to 20 ring carbon atoms of $Ar_{11}$, $Ar_{21}$, $Ar_{31}$ and the substituent of these aryl groups in the formula (2d), a quinoline structure, a quinoxaline structure, a quinazoline structure, an acrylidine structure, a phenanthridine structure, a phthalazine structure, a phenanthroline structure or the like can be given. Of these, a quinoline structure, a quinoxaline structure, a quinazoline structure, a phthalazine structure and a phenanthroline structure are preferable.

A trivalent group induced from the aromatic ring of Ar in the formula (2d) preferably has 6 to 30 carbon atoms, more preferably 6 to 20 carbon atoms and further preferably 6 to 16 carbon atoms.

The trivalent group induced from the heterocyclic aromatic ring of Ar in the formula (2d) preferably contains an atom selected from a nitrogen atom a sulfur atom and an oxygen atom as the hetero atom. More preferably it contains a nitrogen atom.

In the organic EL device of the invention, each organic layer such as the emitting layer or the like can be formed by a dry film forming method such as the vacuum vapor deposition method, the molecular beam epitaxy (MBE) method, sputtering, plasma and ion plating and a coating method such as spin coating, dipping, casting, bar coating, roll coating, flow coating, ink jetting or the like of a solution.

In particular, when an organic EL device is fabricated by using the benzofluoranthene derivative of the invention, the organic compound layer and the emitting layer can be formed not only by deposition but also by a wet method.

Although there are no particular restrictions on the film thickness of each layer of the organic compound layer, it is required to set it to a suitable film thickness. Generally, if the film thickness is too small, pinholes or the like are generated, and a sufficient luminance may not be obtained even though an electric field is applied. On the other hand, if the film thickness is too large, a high voltage is required to be applied in order to obtain a certain optical output, resulting in a poor efficiency. In general, a suitable film thickness is in the range of 5 nm to 10 μm, with the range of 10 nm to 0.2 μm being further preferable.

In the case of the wet film forming method, as the material for an organic EL device, an organic EL material containing solution which contains the benzofluoranthene derivative of the invention and a solvent can be used. It is preferable to use an organic EL material containing solution containing the benzofluoranthene derivative of the invention and at least one selected from the compounds shown by the formulas (2a), (2b), (2c) and (2d).

In this case, an organic EL material forming each layer is dissolved or dispersed in a suitable solvent to prepare a solution containing an organic EL material to form a thin film. Any solvent may be used. Examples of the solvent include halogen-based hydrocarbon-based solvents such as dichloromethane, dichloroethane, chloroform, carbon tetrachloride, tetrachloroethane, trichloroethane, chlorobenzene, chlorotoluene and trifluorotoluene; an ether-based solvent such as dibutyl ether, tetrahydrofuran, tetrahydropyrane, dioxane, anisole and dimethoxyethane, an alcohol-based solvent such as methanol, ethanol, propanol, isopropanol, butanol, pentanol, hexanol, cyclohexanol, methylcellosolve, ethylcellosolve and ethylene glycol, a ketone-based solvent such as acetone, methyl ethyl ketone, diethylketone, 2-hexanone, methylisobutylketone, 2-heptanone, 4-heptanone, diisobutylketone, acetonylacetone, isophorone, cyclohexanone, methylhexanone and acetophenone, a hydrocarbon-based solvent such as benzene, toluene, xylene, ethylbenzene, hexane, cyclohexane, octane, decane and tetralin, an ester-based solvent such as ethyl acetate, butyl acetate and amyl acetate, a branched carbonate ester-based solvent such as dimethyl carbonate, methyl ethyl carbonate and diethyl carbonate, and a cyclic carbonate ester-based solvent such as ethylene carbonate and propylene carbonate. Of these, a hydrocarbon-based solvent or an ether-based solvent such as toluene and dioxane are preferable. Further, these solvents may be used singly or in combination of two or more. Usable solvents are not limited thereto.

In each organic compound layer, a suitable resin or additive may be used for improvement of film-forming properties, prevention of pinhole generation in the film or the like. Usable resins include insulating resins such as polystyrene, polycarbonate, polyarylate, polyester, polyamide, polyurethane, polysulfone, polymethyl methacrylate, polymethyl acrylate and cellulose, and copolymers thereof, photoconductive resins such as poly-N-vinylcarbazole and polysilane, and conductive resins such as polyaniline, polythiophene and polypyrrole. As the additive, antioxidants, UV absorbers, plasticizers or the like can be given.

In order to improve stability to temperature, humidity, atmosphere or the like of the organic EL device of the invention, it is possible to provide a protective layer on the surface of the device, or to protect the entire device with silicone oil, a resin or the like.

In the organic EL device of the invention, it is preferred that a layer selected from a calcogenide layer, a metal halide layer and a metal oxide layer on at least one surface of the pair of electrode.

(Constitution of Organic EL Device)
(1) Structure of Organic EL Device

The representative device structure of the organic EL device of the invention is given below.
(1) Anode/emitting layer/cathode
(2) Anode/hole-injecting layer/emitting later/cathode
(3) Anode/emitting layer/electron-injecting layer/cathode
(4) Anode/hole-injecting layer/emitting layer/electron-injecting layer/cathode
(5) Anode/organic semiconductor layer/emitting layer/cathode
(6) Anode/organic semiconductor layer/electron blocking layer/emitting layer/cathode
(7) Anode/organic semiconductor layer/emitting layer/adhesion-improving layer/cathode
(8) Anode/hole-injecting layer/hole-transporting layer/emitting layer/electron-injecting layer/cathode
(9) Anode/insulating layer/emitting layer/insulating layer/cathode
(10) Anode/inorganic semiconductor layer/insulating layer/emitting layer/insulating layer/cathode
(11) Anode/organic semiconductor layer/insulating layer/emitting layer/insulating layer/cathode
(12) Anode/insulating layer/hole-injecting layer/hole-transporting layer/emitting layer/insulating layer/cathode
(13) Anode/insulating layer/hole-injecting layer/hole-transporting layer/emitting layer/electron-injecting layer/cathode Of these, the structure (8) is preferably used.

The benzofluoranthene derivative of the invention may be used in any of the above-mentioned organic layers. However, it is preferred that it be contained in the emission region or in the hole-transporting region of these constituent elements.

(2) Transparent Substrate

The organic EL device is formed on a transparent substrate. The transparent substrate as referred to herein is a substrate for supporting the organic EL device, and is preferably a flat and smooth substrate having a 400-to-700-nm-visible-light transmittance of 50% or more.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfone, and polysulfone.

(3) Anode

The anode of the organic EL device plays a role for injecting holes into its hole-transporting layer or emitting layer. The anode effectively has a work function of 4.5 eV or more. Indium tin oxide alloy (ITO), tin oxide (NESA), gold, silver, platinum, copper, and the like may be used as the material for the anode. As the anode, in order to inject electrons into the electron-transporting layer or the emitting layer, a material having a small work function is preferable.

The anode can be formed by forming these electrode materials into a thin film by vapor deposition, sputtering or the like.

In the case where emission from the emitting layer is outcoupled through the anode, the transmittance of the anode to the emission is preferably more than 10%. The sheet resistance of the anode is preferably several hundred $\Omega/\square$ or less. The film thickness of the anode, which varies depending upon the material thereof, is usually selected from 10 nm to 1 µm, preferably from 10 to 200 nm.

(4) Emitting Layer

The emitting layer of the organic EL device has the following functions (1), (2) and (3) in combination. That is, (1) Injection function: function of allowing injection of holes from the anode or hole-injecting layer and injection of electrons from the cathode or electron-injecting layer upon application of an electric field (2) Transporting function: function of moving injected carriers (electrons and holes) due to the force of an electric field (3) Emitting function: function of allowing electrons and holes to recombine to emit light Note that electrons and holes may be injected into the emitting layer with different degrees, or the transportation capabilities indicated by the mobility of holes and electrons may differ. It is preferable that the emitting layer move either electrons or holes.

As the method of forming the emitting layer, a known method such as deposition, spin coating, or an LB method may be applied. It is preferable that the emitting layer be a molecular deposition film.

The molecular deposition film as referred to herein means a thin film which is formed by deposition of a raw material compound in the vapor-phase state or a film which is formed by solidification of a raw material compound in the solution state or in the liquid-phase state and is distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like.

In the invention, if desired, known emitting materials other than the emitting materials formed of the compound of the invention having a fluoranthene structure and a fused ring containing compound may be contained in the emitting layer insofar as the object of the invention is not impaired. An emitting layer containing other known emitting materials may be stacked on the emitting layer containing the emitting materials of the invention.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

(5) Hole-Injecting/Transporting Layer (Hole-Transporting Zone)

The hole-injecting/transporting layer is a layer for helping the injection of holes into the emitting layer to transport the holes to a light emitting region. The hole mobility thereof is large and the ionization energy thereof is usually as small as 5.5 eV or less. Such a hole-injecting/transporting layer is preferably made of a material which can transport holes to the emitting layer at a low electric field intensity. The hole mobility thereof is preferably at least $10^{-4}$ cm$^2$/V·second when an electric field of, e.g. $10^4$ to $10^6$ V/cm is applied.

If the benzofluoranthene compound is used in the hole-transporting region, the hole-injecting/transporting layer may be formed by using the benzofluoranthene compound alone or in a mixture with other materials.

As the material for forming the hole-injecting/transporting layer in a mixture with the benzofluoranthene compound of the invention, any materials which have the above preferable properties can be used as the material for forming the hole-injecting/transporting layer without particular limitation. The material for forming the hole-injecting/transporting layer can be arbitrarily selected from materials which have been widely used as a material transporting carriers of holes in photoconductive materials and known materials used in a hole-injecting transporting layer of organic EL devices.

Specific examples thereof include a triazole derivative, an oxadiazole derivative, and an imidazole derivative, a polyarylalkane derivative, a pyrazoline derivative, and a pyrazolone derivative, a phenylene diamine derivative, an arylamine derivative, an amino-substituted chalcone derivative, an oxazole derivative, a styrylanthracene derivative, a fluorenone derivative, a hydrazone derivative, a stilbene derivative, a silazane derivative, a polysilane-based copolymer and an aniline-based copolymer.

Although the above-mentioned materials are used as the material for the hole-injecting/transporting layer, a porphyrin compound, an aromatic tertiary amine compound and a styrylamine compound are preferable, with an aromatic tertiary amine compound being preferable.

It is preferable to use a compound having two fused aromatic rings in the molecule thereof, for example, 4,4'-bis(N-(1-naphthyl)-N-phenylamino)biphenyl (abbreviated by NPD, hereinafter), and 4,4',4"-tris(N-(3-methylphenyl)-N-phenylamino)triphenylamine (abbreviated by MTDATA, hereinafter) wherein three triphenylamine units are linked in a star-burst form.

In addition to the aromatic dimethylidene type compounds mentioned above as the material for an emitting layer, inorganic compounds, p-type Si and p-type SiC can also be used as the material of the hole-injecting layer.

The hole-injecting/transporting layer can be formed from the above-mentioned compounds by a known method such as vacuum vapor deposition, spin coating, casting or LB technique. The film thickness of the hole-injecting/transporting layer is not particularly limited, and is usually from 5 nm to 5 µm.

(6) Electron-Injecting Layer

The electron-injecting layer is a layer which assists injection of electrons into the emitting layer, and exhibits a high electron mobility. An adhesion-improving layer is a type of the electron-injecting layer formed of a material which exhibits excellent adhesion to the cathode. The material used in the electron-injecting layer is preferably a metal complex of 8-hydroxyquinoline or a derivative thereof.

As specific examples of a metal complex of an 8-hydroxyquinoline or a derivative thereof, metal chelate oxynoid compounds including a chelate of oxine (generally, 8-quinolinol or 8-hydroxyquinoline) can be given.

For example, Alq described as the emitting material can be used for the electron-injecting layer.

An electron-transmitting compound of the following formula can be given as the oxadiazole derivative.

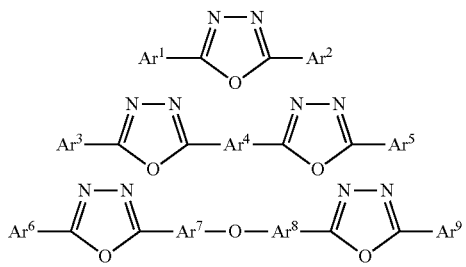

wherein $Ar^1$, $Ar^2$, $Ar^3$, $Ar^5$, $Ar^6$, and $Ar^9$ are independently substituted or unsubstituted aryl groups and may be the same or different. $Ar^4$, $Ar^7$, and $Ar^8$ are independently substituted or unsubstituted arylene groups and may be the same or different.

The electron-transmitting compound is preferably one from which a thin film can be formed.

A preferred embodiment of the invention is a device containing a reducing dopant in an electron-transferring region or in an interfacial region between the cathode and the organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal organic complexes, alkaline earth metal organic complexes, and rare earth metal organic complexes.

More specific examples of the preferred reducing dopants include at least one alkali metal selected from the group consisting of Li (work function: 2.9 eV), Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). One having a work function of 2.9 eV or less is particularly preferable. Among these, a more preferable reducing dopant is at least one alkali metal selected from the group consisting of K, Rb and Cs. Even more preferable is Rb or Cs. Most preferable is Cs. These alkali metals are particularly high in reducing ability. Thus, the addition of a relatively small amount thereof to an electron-injecting zone improves the luminance of the organic EL device and makes the lifetime thereof long. As a reducing agent having a work function of 2.9 eV or less, combinations of two or more alkali metals are preferable, particularly combinations including Cs, such as Cs and Na, Cs and K, Cs and Rb, or Cs, Na and K are preferable. The combination containing Cs makes it possible to exhibit the reducing ability efficiently. The luminance of the organic EL device can be improved and the lifetime thereof can be made long by the addition thereof to its electron-injecting zone.

In the invention, an electron-injecting layer made of an insulator or a semiconductor may further be provided between a cathode and an organic layer. By forming the electron-injecting layer, current leakage can be effectively prevented and electron-injecting properties can be improved. As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved. Specifically preferable alkali metal calcogenides include $Li_2O$, $K_2O$, $Na_2S$, $Na_2Se$ and $Na_2O$ and preferable alkaline earth metal calcogenides include CaO, BaO, SrO, BeO, BaS and CaSe. Preferable halides of alkali metals include LiF, NaF, KF, LiCl, KCl and NaCl. Preferable halides of alkaline earth metals include fluorides such as $CaF_2$, $BaF_2$, $SrF_2$, $MgF_2$ and $BeF_2$ and the halides other than the fluorides.

Semiconductors forming an electron-transporting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-transporting layer is preferably a microcrystalline or amorphous insulating thin film. When the electron-transporting layer is formed of the insulating thin films, more uniformed thin film is formed whereby pixel defects such as a dark spot are decreased. Examples of such an inorganic compound include the above-mentioned alkali metal calcogenides, alkaline earth metal calcogenides, halides of alkali metals, and halides of alkaline earth metals.

(7) Cathode

As the cathode, a metal having a small work function (4 eV or less), an alloy, an electroconductive compound or a mixture thereof are used as an electrode material in order to inject electrons to electron-injecting/transporting layer. Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by vapor deposition, sputtering or some other method.

In the case where light is emitted from the emitting layer through the cathode, the cathode preferably has a light transmittance of larger than 10%.

The sheet resistance of the cathode is preferably several hundreds Ω/□ or less, and the film thickness thereof is usually from 10 nm to 1 μm, preferably from 50 to 200 nm.

(8) Insulating Layer

In the organic EL device, pixel defects based on leakage or a short circuit are easily generated since an electric field is applied to the super thin film. In order to prevent this, it is preferred to insert an insulating thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide.

A mixture or laminate thereof may be used.

(9) Method for Forming an Organic EL Device

The organic EL device can be fabricated by forming an anode, an emitting layer, optionally a hole-injecting layer, and optionally an electron-injecting layer, and further forming a cathode using the materials and methods exemplified above. The organic EL device can be fabricated in the order reverse to the above, i.e., the order from a cathode to an anode.

An example of the fabrication of the organic EL device will be described below wherein the following layers are successively formed on a transparent substrate: anode/hole-injecting layer/emitting layer/electron-injecting layer/cathode.

First, a thin film made of an anode material is formed into a thickness of 1 μm or less, preferably 10 to 200 nm on an appropriate transparent substrate by vacuum vapor deposition, sputtering or some other method, thereby forming an anode. Next, a hole-injecting layer is formed on this anode. As described above, the hole-injecting layer can be formed by vacuum vapor deposition, spin coating, casting, LB technique, or some other method. Vacuum vapor deposition is preferred since a homogenous film is easily obtained and pinholes are not easily generated. In the case where the hole-injecting layer is formed by vacuum vapor deposition, conditions for the deposition vary depending upon a compound used (a material for the hole-injecting layer), a desired crystal structure or recombining structure of the hole-injecting layer, and others. In general, the conditions are preferably selected from the following: deposition source temperature of 50 to 450° C., vacuum degree of $10^{-7}$ to $10^{-3}$ torr, deposition rate of 0.01 to 50 nm/second, substrate temperature of −50 to 300° C., and film thickness of 5 nm to 5 μm.

The emitting layer can also be formed on the hole-injecting layer by making a desired organic luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-injecting layer.

Next, an electron-injecting layer is formed on this emitting layer. Like the hole-injecting layer and the emitting layer, the layer is preferably formed by vacuum vapor deposition because a homogenous film is required to be obtained. Conditions for the deposition can be selected from conditions similar to those for the hole-injecting layer and the emitting layer.

The compound of the invention, depending on the layer where it is contained, i.e. the emission region or the hole-transporting region, can be co-deposited with other materials when vacuum vapor deposition is used. If the spin coating method is used, it can be contained by mixing with other materials.

Lastly, a cathode is stacked thereon to obtain an organic EL device.

The cathode is made of a metal, and deposition or sputtering may be used. However, vacuum vapor deposition is preferred in order to protect underlying organic layers from being damaged when the cathode film is formed.

For the organic EL device fabrication that has been described above, it is preferred that the formation from the anode to the cathode be continuously carried out, using only one vacuuming operation.

The film thickness of each of the organic layers in the organic EL device of the invention is not particularly limited. In general, defects such as pinholes are easily generated when the film thickness is too small. Conversely, when the film thickness is too large, a high applied voltage becomes necessary, leading to low efficiency. Usually, the film thickness is preferably in the range of several nanometers to one micrometer.

If a DC voltage is applied to the organic EL device, emission can be observed when the polarities of the anode and the cathode are positive and negative, respectively, and a DC voltage of 5 to 40 V is applied. When a voltage with an opposite polarity is applied, no electric current flows and hence, emission does not occur. If an AC voltage is applied, uniform emission can be observed only when the cathode and the anode have a positive polarity and a negative polarity, respectively. The waveform of the AC applied may be arbitrary.

(Application of Organic EL Device)

The organic EL device of the invention can be applied to products which require high luminous efficiency even at a low driving voltage. As application examples, a display apparatus, a display, a lighting apparatus, a printer light source, and the back light of a liquid crystal display, etc. can be given. It can also be applied to fields such as a sign, a signboard and interiors. As a display apparatus, an energy-saving, highly visible flat panel display can be given. Moreover, as a printer light source, the organic EL device can be used as a light source of a laser beam printer. Moreover, the volume of an apparatus can be reduced sharply by using the device of the invention. As for the lighting apparatus or the back light, energy-saving effects can be expectable by using the organic EL device of the invention.

EXAMPLES

The invention will be explained in detail with reference to Examples, which should not be construed as limiting the scope of the invention.

Example 1

Preparation of Compound D-1

Under an argon atmosphere, 30.0 g (111 mmol) of a commercially available intermediate 1, 41.3 g (222 mmol) of 1,2-dibromoethylene, 633 mg (3.33 mmol) of paratoluenesulfonic acid and 150 mL of xylene were placed and stirred at 100° C. for 18 hours. After cooling to room temperature, the reaction solution was concentrated, methanol was added, and the deposited solids were filtered. The deposited solids were dissolved in toluene with heating to allow them to be concentrated, methanol was added to filter the deposited solids out, and the solids thus filtered were dried under a reduced pressure, whereby 17.0 g of yellowish while solids were obtained. As a result of the FD-MS (field desorption mass spectroscopy) analysis, the solids were identified as the intermediate 2.

Intermediate 1

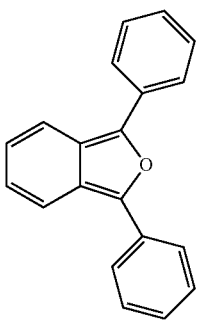

Intermediate 2

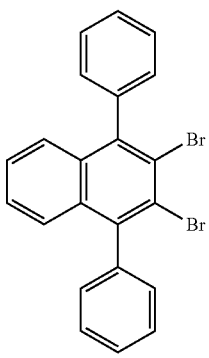

Under an argon atmosphere, 6.0 g (13.7 mmol) of the resulting intermediate 2, 3.6 g (16.4 mmol) of the intermediate 3, 2.5 g (2.74 mmol) of tris(dibenzylideneacetone)dipalladium, 3.1 g (11.0 mmol) of tricyclohexylphosphine, 14.6 g (95.9 mmol) of diazabicycloundecene and 150 mL of N,N-dimethylformamide were placed, followed by stirring at 155° C. for 18 hours. After cooling to the room temperature, the reaction liquid was concentrated and purified by the short column chromatography (toluene). The resulting solids were re-crystallized twice with toluene, dried under reduced pressure, whereby 2.1 g of yellowish white solids were obtained. As a result of the FD-MS analysis, the resulting solids were identified as the compound D-1.

Intermediate 3

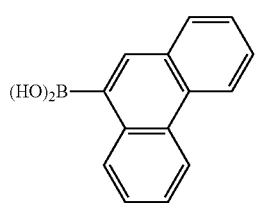

Preparation of Compound D-2

The compound D-2 was synthesized in the same manner as in Example 1, except that the intermediate 4 was used instead of the intermediate 3. The compound D-2 was identified by the FD-MS analysis.

Intermediate 4

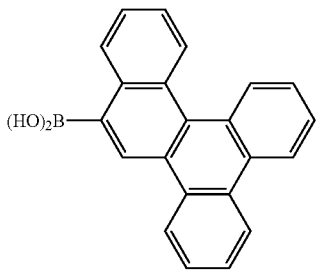

Example 3

Preparation of Compound D-3

The compound D-3 was synthesized in the same manner as in Example 1, except that the intermediate 5 was used instead of the intermediate 3. The compound D-3 was identified by the FD-MS analysis.

Intermediate 5

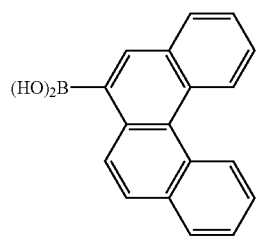

Example 4

Preparation of Compound D-4

The compound D-4 was synthesized in the same manner as in Example 1, except that the intermediate 6 was used instead of the intermediate 3. The compound D-4 was identified by the FD-MS analysis.

Intermediate 6

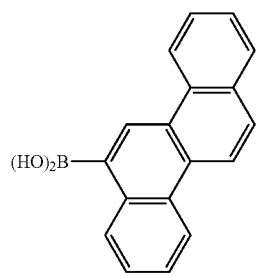

Example 5

Preparation of Compound D-5

The compound D-5 was synthesized in the same manner as in Example 1, except that the intermediate 7 was used instead of the intermediate 3. The compound D-5 was identified by the FD-MS analysis.

Intermediate 7

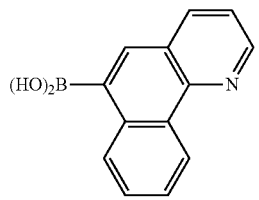

Example 6

Fabrication of Organic EL Device

On a glass substrate with a dimension of 25 mm×75 mm×1.1 mm, a 120 nm-thick transparent electrode formed of indium tin oxide was provided. This glass substrate was subjected to ultrasonic cleaning with isopropyl alcohol, and to VV/ozone cleaning procedures. Next, the glass substrate with a transparent electrode was mounted in a substrate holder in a vacuum vapor deposition apparatus, and the vacuum degree of the vacuum chamber was reduced to $1 \times 10^{-3}$ Pa.

First, a 60 nm-thick film formed of N',N'''-bis[4-(diphenylamino)phenyl]-N',N'''-diphenylbiphenyl-4,4'-diamine was deposited at a deposition speed of 2 nm/sec on the surface on which a transparent electrode was formed so as to cover the transparent electrode. This layer functions as a hole-injecting layer. Then, a 20 nm-thick film formed of N,N,N',N'-tetra(4-biphenylyl)benzidine was deposited on the hole-injecting layer at a deposition speed of 2 nm/sec. This film functions as a hole-transporting layer.

On the hole-transporting layer, compound 2a'-55 (Emitting material 1) and compound D-1 (Emitting material 2) prepared in Example 1 were co-deposited at a deposition speed of 2 nm/sec and 0.2 nm/sec, respectively such that the film thickness became 40 nm and the weight ratio of the compound 2a'-55 to the compound D-1 became 40:2. This film functions as the emitting layer.

On the emitting layer, tris(8-hydroxyquinolinolato) aluminum was deposited at a deposition speed of 2 nm/sec in a film thickness of 20 nm, whereby an electron-transporting layer was formed. Further, lithium fluoride was deposited at a deposition speed of 0.1 nm/sec in a film thickness of 1 nm, whereby an electron-injecting layer was formed. Finally, aluminum was deposited at a deposition speed of 2 nm/sec in a film thickness of 200 nm to form a cathode layer, whereby an organic EL device was produced.

[Evaluation of Organic EL Device]

The organic EL device obtained was subjected to current test. At a driving voltage of 6.2 V, a luminous efficiency was 3.5 cd/A. The emission peak wavelength (EL λmax) and chromaticity were measured, and it was confirmed that it emitted blue light. The organic EL device was subjected to constant current driving at an initial luminance of 100 cd/m². The organic EL device had a half life of 10,000 hours, which was sufficiently practical. The results are shown in Table 1.

Examples 7 to 13 and Comparative Example 1

An organic EL device was fabricated and evaluated in the same manner as in Example 6, except that the combination of the emitting material 1 and the emitting material 2 was changed to the combination of the emitting materials shown in Tables 1 and 2. The results are shown in Tables 1 and 2.

The organic EL devices of Examples 7 to 13 emitted blue light.

The emitting materials 1 used in Examples 7 to 13 and Comparative Example 1 are shown below.

2a'-55

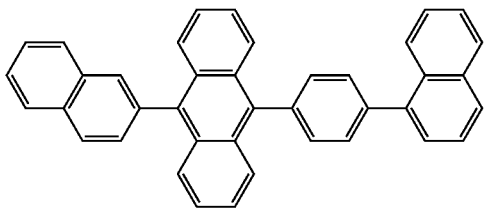

2a'-59

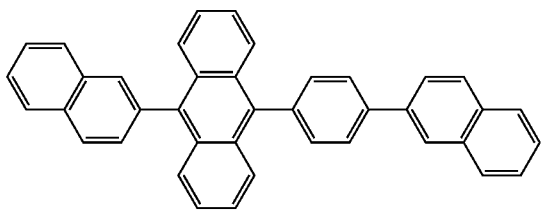

2a-7

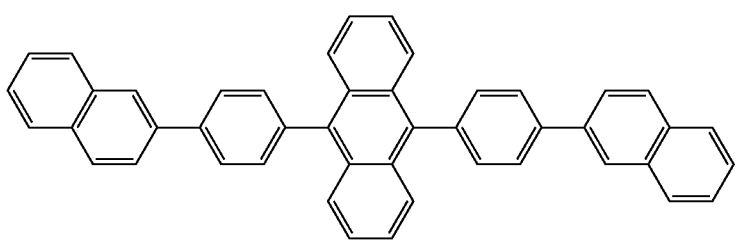

2b-42

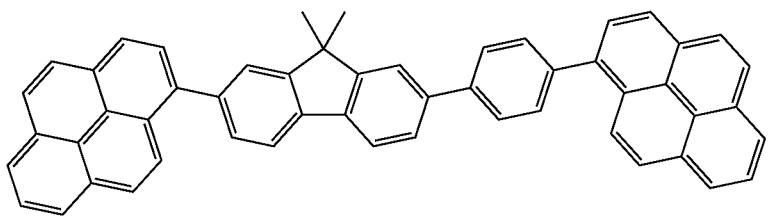

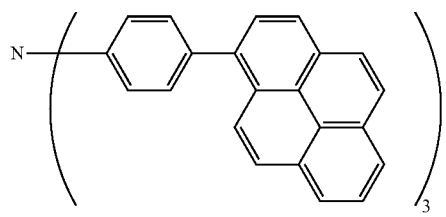

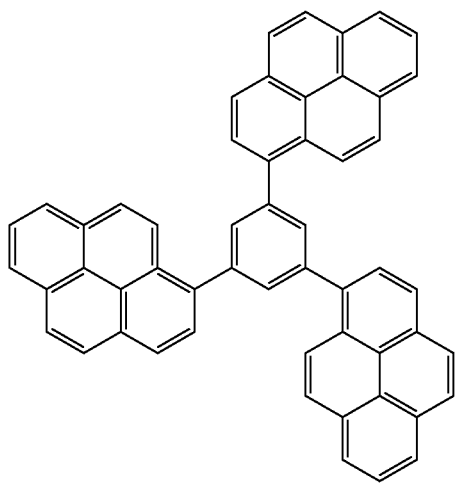

The compound H-1 used in Comparative Example 1 (UV (PhMe); λmax, 410, FL(PhMe); λmax, 424 nm) is a fluoranthene compound represented by the following formula.

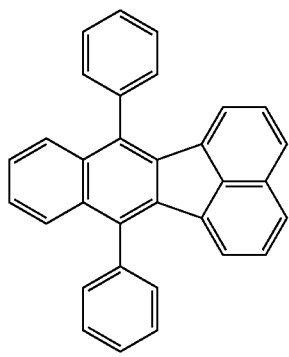

TABLE 1

|  | Example 6 | Example 7 | Example 8 | Example 9 | Example 10 |
|---|---|---|---|---|---|
| Emitting material 1 | 2a'-55 | 2a'-55 | 2a'-55 | 2a'-59 | 2a-7 |
| Emitting material 2 | D-1 | D-2 | D-3 | D-4 | D-5 |
| Driving voltage [V] | 6.2 | 6.1 | 6.1 | 6.2 | 6.4 |
| EL λ max [nm] | 443 | 449 | 450 | 444 | 444 |
| Luminous efficiency [cd/A] | 3.5 | 4.5 | 4.4 | 4.2 | 4.0 |
| Half life [hour] | 10000 | 14000 | 13000 | 13000 | 12000 |

TABLE 2

|  | Example 11 | Example 12 | Example 13 | Com. Ex. 1 |
|---|---|---|---|---|
| Emitting material 1 | 2b-42 | 2c-1 | 2d-1 | 2a'-55 |
| Emitting material 2 | D-2 | D-4 | D-5 | H-1 |

TABLE 2-continued

|  | Example 11 | Example 12 | Example 13 | Com. Ex. 1 |
|---|---|---|---|---|
| Driving voltage [V] | 6.3 | 6.2 | 6.4 | 6.3 |
| EL λ max [nm] | 453 | 446 | 442 | 448.0 |
| Luminous efficiency [cd/A] | 4.5 | 4.0 | 3.9 | 1.5 |
| Half life [hour] | 13000 | 9000 | 8500 | 2000 |

INDUSTRIAL APPLICABILITY

An organic EL device using the benzofluoranthene derivative of the invention as a material for an organic EL device, in particular, an emitting material for an organic EL device, has a high luminous efficiency and a long life.

The organic EL device of the invention is highly practical, and is effective as a light source such as a planar emitting body of a wall-hanging television and a backlight of display. The benzofluoranthene derivative of the invention can be used as a hole-injecting/transporting material of an organic EL device, further as a carrier-transporting material of an electrophotographic photoreceptor or an organic semiconductor.

The contents of the above-described documents are herein incorporated by reference in its entirety.

The invention claimed is:

1. An organic electroluminescence device comprising one or more organic thin layers comprising an emitting layer, between a cathode and an anode, wherein
at least one of the organic thin layers comprises a material for an organic electroluminescence comprising a benzofluoranthene derivative represented by the following formula (1):

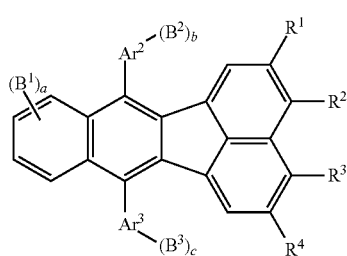
(1)

wherein $B^1$ to $B^3$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxyl group, a substituted or unsubstituted silyl group, a carboxy group, or a halogen atom;
  a is an integer of 0 to 4, b and c are independently an integer of 0 to 5,
  when a is 2 or more, $B^1$s may be the same or different, and they may be bonded together to form a saturated or unsaturated ring,
  when b is 2 or more, $B^2$s may be the same or different, and they may be bonded together to form a saturated or unsaturated ring,
  when c is 2 or more, $B^3$s may be the same or different, and they may be bonded together to form a saturated or unsaturated ring,
  $Ar^2$ and $Ar^3$ are independently a substituted or unsubstituted aryl group having 5 to 50 ring carbon atoms, or a substituted or unsubstituted heterocyclic group having 5 to 50 ring carbon atoms,
  $R^1$ to $R^4$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxy group, a substituted or unsubstituted silyl group, a carboxy group, or a halogen atom;
  at least one pair of "$R^1$ and $R^2$" and "$R^3$ and $R^4$" is bonded together to form a ring represented by the following formula (2),
  when both "$R^1$ and $R^2$" and "$R^3$ and $R^4$" form a ring, the rings may be the same or different,

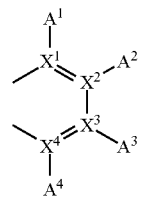
(2)

wherein $A^1$ to $A^4$ are independently a hydrogen atom, a substituted or unsubstituted alkyl group having 1 to 50 carbon atoms, a substituted or unsubstituted aryl group having 5 to 50 ring carbon atoms, a substituted or unsubstituted heterocyclic group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 carbon atoms, a cyano group, a nitro group, a hydroxyl group, a substituted or unsubstituted silyl group, a carboxy group, or a halogen atom;
  among $A^1$ to $A^4$, adjacent groups may be bonded to form a saturated or unsaturated ring, and the ring may have a substituent, and
  $X^1$ to $X^4$ are independently a carbon atom or a nitrogen atom, and when any one of $X^1$ to $X^4$ is a nitrogen atom, $A^1$ to $A^4$ which bond to the one of $X^1$ to $X^4$ do not exist.

2. The organic electroluminescence device according to claim 1 wherein the emitting layer comprises the material for an organic electroluminescence device, and
  the content of the benzofluoranthene derivative is 0.1 to 20 wt %.

3. The organic electroluminescence device according to claim 1, which can emit blue light.

* * * * *